United States Patent [19]
Dean et al.

[11] Patent Number: 6,153,599
[45] Date of Patent: *Nov. 28, 2000

[54] METHOXYETHOXY OLIGONUCLEOTIDES FOR MODULATION OF PROTEIN KINASE C EXPRESSION

[75] Inventors: Nicholas M. Dean, Olivenhain, Calif.; Pierre Martin, Rheinfelden; Karl-Heinz Altmann, Reinach, both of Switzerland

[73] Assignees: ISIS Pharmaceuticals, Inc., Carlsbad, Calif.; Novartis AG, Basel, Switzerland

[ * ] Notice: This patent is subject to a terminal disclaimer.

[21] Appl. No.: 09/117,901

[22] PCT Filed: Feb. 13, 1997

[86] PCT No.: PCT/US97/02003

§ 371 Date: Jan. 19, 1999

§ 102(e) Date: Jan. 19, 1999

[87] PCT Pub. No.: WO97/29780

PCT Pub. Date: Aug. 21, 1997

Related U.S. Application Data

[63] Continuation-in-part of application No. 08/478,178, Jun. 7, 1995, Pat. No. 5,882,927, which is a continuation-in-part of application No. 08/089,996, Jul. 9, 1993, Pat. No. 5,703,054, which is a continuation-in-part of application No. 07/852,852, Mar. 16, 1992, abandoned.

[51] Int. Cl.$^7$ .......................... C07H 21/04; A61K 48/00; C12Q 1/68; C12N 5/00
[52] U.S. Cl. .......................... 514/44; 536/23.1; 536/24.3; 536/24.5; 435/6; 435/91.1; 435/325; 435/375
[58] Field of Search .............................. 514/44; 536/24.5, 536/25.33, 25.34, 22.1, 23.1, 23.7, 24.32; 435/375, 6, 91.1, 325, 91.2

[56] References Cited

U.S. PATENT DOCUMENTS

| | | | |
|---|---|---|---|
| 4,511,713 | 4/1985 | Miller et al. | 435/6 |
| 4,806,463 | 2/1989 | Goodchild et al. | 435/5 |
| 5,004,810 | 4/1991 | Draper | 536/24.5 |
| 5,034,506 | 7/1991 | Summerton et al. | 528/391 |
| 5,087,617 | 2/1992 | Smith | 514/44 |
| 5,098,890 | 3/1992 | Gerwitz et al. | 514/44 |
| 5,135,917 | 8/1992 | Burch | 514/44 |
| 5,138,045 | 8/1992 | Cook et al. | 536/24.5 |
| 5,166,195 | 11/1992 | Ecker | 514/44 |
| 5,194,428 | 3/1993 | Agrawal et al. | 514/44 |
| 5,225,326 | 7/1993 | Bresser et al. | 435/6 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,585,479 | 12/1996 | Hoke et al. | 536/24.5 |
| 5,703,054 | 12/1997 | Bennett et al. | 514/44 |
| 5,882,927 | 3/1999 | Bennett et al. | 435/375 |
| 5,948,898 | 2/1996 | Dean et al. | 536/23.5 |

FOREIGN PATENT DOCUMENTS

| | | |
|---|---|---|
| WO 93/13121 | 7/1993 | WIPO . |
| WO 93/20101 | 10/1993 | WIPO . |
| WO 94/29455 | 12/1994 | WIPO . |

OTHER PUBLICATIONS

Crook, S., Basic Principles of Antisense Therapeutics, Springer–Verlag Berlin Heidelberg New York, Jul. 1998.

Gura T., Antisense Has Growing Pains, Science, vol. 270, pp. 575–577, Oct. 1995.

Crooke, S. et al., Antisense '97: A roundtable on the state of the industry, Nature Biotechnology, vol. 15, p.522, Jun. 1997.

Branch, A., A Good antisense molecule is hard to find, TIBS vol. 23, pp 47–49, Feb. 1998.

Ahmad et al., "Antisense Expression of Protein Kinase Cα Inhibits the Growth and Tumorigenicity of Human Glioblastoma Cells", *Neurosurg.*, 1994, 35, 904–908.

Bacher, N. et al., "Isolation and Characterization of PKC–L, A New Member of the Protein Kinase C–Related Gene Family Specifically Expressed in Lung, Skin, and Heart", *Mol. Cell. Biol.*, 1991, 11, 126–133.

Ballester, R. et al., "Fate of Immunoprecipitable Protein Kinase C in GH$_3$ Cells Treated with Phorbol 12–Myristate 13–Acetate", *J. Biol. Chem.*, 1985, 260(28),15194–15199.

Baxter et al., "PKC–episilon is involved in granulocyte–macrophage colong–stimulating factor signal transduction: Evidence from microphysiometry and antisense oligonucleotide experiments", *Biochemistry*, 1992, 31, 10950–10954.

Berkowitz, P.T. et al., "Synthesis of 1,2–Dihydro–1–(2–deoxy–β–D–erythro–pentofuranosyl)–2–oxopyrizine 4–Oxide, a Potent Analog of Deoxyuridine", *J. Med. Chem.*, 1973, 16, 813–814.

Borek, C. et al., "Long–chain (sphingoid) bases inhibit multistage carcinogenesis in mouse C3H/10T½ cells treated with radiation and phorbol 12–myristate 13–acetate", *Proc. Natl. Acad. Sci.*, 1991, 88, 1953–1957.

Brandt, S.J. et al., "Distinct Patterns of Expression of Different protein Kinase C mRNAs in Rat Tissues", *Cell*, 1987, 49, 57–63.

Coussens et al., "Multiple, Distinct Forms of Bovine and Human Protein Kinase C Suggest Diversity in Cellular Signaling Pathways", *Science*, 1986, 233, 859–866.

Endo, et al., "Cell Membrane Signaling as Target in Cancer Therapy: Inhibitory Effect of N,N–Dimethyl and N,N,N–Trimethyl Sphingosine Derivatives on In Vitro and In Vivo Growth of Human Tumor Cells in Nude Mice", *Cancer Research*, 1991, 51, 1613–1618.

(List continued on next page.)

Primary Examiner—George C. Elliott
Assistant Examiner—Janet Epps
Attorney, Agent, or Firm—Woodcock Washburn Kurt MacKiewicz & Norris LLP

[57] ABSTRACT

Compositions and methods are provided for modulating the expression of protein kinase C. Oligonucleotides are provided which are targeted to nucleic acids encoding PKC. The oligonucleotides contain a methoxyethoxy (—O—CH$_2$CH$_2$OCH$_3$) modification at the 2' position of at least one nucleotide. Methods of inhibiting PKC expression and methods of treating conditions associated with expression of PKC using oligonucleotides of the invention are disclosed.

9 Claims, 7 Drawing Sheets

OTHER PUBLICATIONS

Farese et al., "Antisense DNA downregulates protein kinase C isozymes (beta and alpha) and insulin–stimulated 2–deoxyglucose uptake in rat adipocytes", *Antisense Res. Dev.*, 1991, 1(1), 35–42.

Finkenzeller, G., "Sequence of Human Protein Kinase C α", *Nucleic Acids Research*, 1990, 18(8), 2183.

Gescher, A. et al., "Protein Kinase C–A Novel Target for Rational Anti–Cancer Drug Design", *Anti–Cancer Drug Design*, 1989, 4, 93–105.

Godson, et al., "Inhibition of Expression of Protein Kinase C α by Antisense cDNA Inhibits Phorbol Ester–Mediated Archidonate Release", *J. Biol. Chem.*, 1993, 268, 11946–11950.

Hackh's Chemical Dictionary, Grant, et al. (ed.), McGraw–Hill Book Company, New York, p. 312.

Hegemann, L. et al., *Pharmacology of the Skin*, H. Mukhtar (ed.), CRC press, Boca Raton, FL, 1992, pp. 357–368.

Hidaka, H. et al., "Pharmacology of the isoquinoline sulfonamide protein kinase C inhibitors", *TIPS*, 1987, 8, 162–164.

Maister, *Bioworld Today*, Apr. 29, 1994, p. 3.

Kubo, K. et al., "Primary structures of human protein kinase CBI and BII differ only in their C–terminal sequences", *FEBS Letters*, 1987, 223(1), 138–142.

Krug, E. et al., "Evidence for increased synthesis as well as increased degradation of protein kinase C after treatment of human ostersarcoma cells with phorbol ester", *J. Biological Chemistry*, 1987, 262(24), 11852–11856.

Standaert et al., *J. Cellular Biochem.*, 1991, (Keystone Symposia on Molecular and Cellular Biology, Jan. 18–25), Suppl. 15B, p.26, abstract CA 211.

Maier, J.A.M. et al., "An Oligomer Targeted against Protein Kinase Cα Prevents Interleuken–1α Induction of Cyclooxygenase Expression in Human Endothelial Cells", *Exp. Cell Res.*, 1993, 205, 52–58.

Marcus–Sekura, C.J., "Techniques for Using Antisense Oligodeosyribonucleotides to Study Gene Expression", *Analyt. Biochem.*, 1988, 172, 289–295.

Nielsen, P.E. et al., "Sequence–Selective Recognition of DNA by Strand Displacement with a Thymine–Substituted Polyamide", *Science*, 1991, 254, 1497–1500.

Nishizuka, Y., "The Molecular Heterogeneity of Protein Kinase C and its Implications for Cellular Regulation", *Nature*, 1988, 334:661–665.

Osada, S. et al., "A phorbol ester receptor/protein kinase, nPKCη, a new member of the protein kinase C family predominantly expressed in lung and skin", *J. Biol. Chem.*, 1990, 265(36), 22434–22440.

Parker et al., "The complete primary stucture of protein kinase c—the major phorbol ester receptor", *Science*, 1986, 233, 853–866.

Rothenberg, M. et al., "Oligodeoxynucleotides as Anti–Sense Inhibitors of Gene Expression: Therapeutic Implications", *J. Natl. Cancer Inst.*, 1989, 81, 1539–1544.

Sakanoue, Y. et al., "Protein Kinase C Activity as Marker for Colorectal Cancer", *Int. J. Cancer*, 1991, 48, 803–806.

Sambrook et al. (eds.), *Molecular Cloning: A Laboratory Manual*, Cold Spring Harbor Laboratory Press, 1989, vol. 2, p. 10.59.

Simons, M. et al., "Antisense c–myb oligonucleotides inhibit intimal arterial smooth muscle cell accumulation in vivo", *Nature*, 1992, 359, 67–70.

Catalog of Products for DNA Research, Glen Research, Sterling, VA, 1993, p. 21.

Watson, J.D. et al., "The Two Chains of the Double Helix Have Complementary Sequences", 1988, *Molecular Biology of the Gene*, Benjamin/Cummings Publishing Co., Inc., Menlo Park, CA, 241.

Webster's II New Riverside University Dictionary, Soukkhanov et al., (Eds.), Houghton Mifflin Company, Boston, MA, 1984, p. 68.

Weinstein, I.B., "Cancer Prevention: Recent Progress and Future Opportunities", *Cancer Research*, 1991, 51, 5080s–5085s.

Young, S. et al., "Down–regulation of protein kinase C is due to an increased rate of degradation", *Biochem.*, 1987, 244, 775–779.

Zon, G., "Oligonucleotide Analogues as Potential Chemotherapeutic Agents", *Pharm. Res.*, 1988, 5, 539–547.

Greenberg, M.E. in *Current Protocols in Molecular Biology*, Ausubel et al. (Eds.), John Wiley & Sons, NY, 1987.

Kawasaki et al., "Synthesis and Biophysical Studies of 2'–dRIBO–F Modified Oligonucleotides", Conference on Nucleic Acid Therapeutics, Clearwater, FL, Jan., 1991.

Boyce et al., *Neurosci. Res. Commun.*, 1996, 18(3), 195–201.

Dean et al., *Proc. Annu. Meet. Assoc. Cancer Res.*, 1995, 36, 413, Abstract 2460.

Gura, T., "Antisense has Growing Pains", *Science*, 1995, 270, 575–577.

Henderson, C.W. (Publ.), *Infectious Disease Weekly*, Oct. 23, 1995.

Martin, P., "Ein neuer Zugang zu 2'–O–Alkylribonucleosiden und Eigenschaften deren Oligonucleotide", *Helvetica Chemica Acta*, 1995, 78, 486–504.

Ono, Y. et al., "The Structure, Expression, and Properties of Additional Members of the Protein Kinase C Family", *J. Biol. Chem.*, 1988, 263, 6927–6932.

Orkin et al., "Report and Recommendations of the Panel to Assess the NIH Investment in Research on Gene Therapy", Dec. 7, 1995.

PR Newswire Association, Inc., PR Newswire, Aug. 1, 1996, p. 0801LATH014.

Uhlmann, E. et al., "Antisense Oligonucleotides: A New Therapeutic Principle", *Chem. Reviews*, 1990, 90, 544–584.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 20 bases
      (B) TYPE: nucleic acid
      (C) STRANDEDNESS: single
      (D) TOPOLOGY: linear (xi) SEQUENCE DESCRIPTION: SEQ ID NO:1:

GTTCTCGCTG GTGAGTTTCA      20

METHOXYETHOXY OLIGONUCLEOTIDES FOR MODULATION OF PROTEIN KINASE C EXPRESSION

CROSS REFERENCE TO RELATED APPLICATIONS

This application is a continuation-in-part of U.S. patent application Ser. No. 08/478,178, filed Jun. 7, 1995, now U.S. Pat. No. 5,882,927, which is a continuation-in-part of U.S. patent application Ser. No. 08/089,996, filed Jul. 9, 1993, now U.S. Pat. No. 5,703,054, which in turn is a continuation-in-part of U.S. patent application Ser. No. 07/852,852 filed Mar. 16, 1992, now abandoned.

FIELD OF THE INVENTION

This invention relates to compositions and methods for modulation of the expression of protein kinase C. In particular, this invention relates to antisense oligonucleotides specifically hybridizable with nucleic acids encoding protein kinase C. These oligonucleotides have been found to modulate the expression of protein kinase C. These compositions and methods can be used diagnostically or therapeutically.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells (Gescher et al., *Anti-Cancer Drug Design* 4:93–105 (1989)). Phorbols capable of tumor production can mimic the effect of DAG in activating PKC, suggesting that these tumor promoters act through PKC and that activation of this enzyme is at least partially responsible for the resulting tumorigenesis (Parker et al., *Science* 233:853–866 (1986)).

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer (Weinstein, *Cancer Res.* (*Suppl.*) 51:5080s–5085s (1991)). It has also been demonstrated that a greater proportion of the PKC in the colonic mucosa of patients with colorectal cancer is in an activated state compared to that of patients without cancer (Sakanoue et al., *Int. J. Cancer* 48:803–806 (1991)).

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo (Endo et al., *Cancer Research* 51:1613–1618 (1991); Borek et al., *Proc. Natl. Acad. Sci.* 88:1953–1957 (1991)). A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs (Gescher, A. and Dale, I. L., *Anti-Cancer Drug Design*, 4:93–105 (1989)).

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis (Hegemann, L. and G. Mahrle, *Pharmacology of the Skin*, H. Mukhtar, ed., p. 357–368, CRC Press, Boca Raton, Fla., 1992).

The oligonucleotides of the invention are believed to be useful in the therapeutic treatment of diseases associated with PKC. Such diseases include hyperproliferative and inflammatory conditions including psoriasis, tumors and cancers, for example glioblastoma, bladder cancer, skin cancer, breast cancer, lung cancer and colon cancer.

PKC is not a single enzyme, but a family of enzymes. At the present time at least seven isoforms (isozymes) of PKC have been identified: isoforms $\alpha$, $\beta$, and $\gamma$ have been purified to homogeneity, and isoforms $\delta$, $\epsilon$, $\zeta$ and $\eta$ have been identified by molecular cloning. These isozymes have distinct patterns of tissue and organ localization (see Nishizuka, *Nature*, 334:661–665 (1988) for review) and may serve different physiological functions.

It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin (Hegemann, L. and G. Mahrle, *Pharmacology of the Skin*, H. Mukhtar, ed., p. 357–368, CRC Press, Boca Raton, Fla. 1992).

Although numerous compounds have been identified as PKC inhibitors (see Hidaka and Hagiwara, *Trends in Pharm. Sci.* 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the CAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases (Gescher, *Anti-Cancer Drug Design* 4:93–105 (1989)). Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and in diagnosis and treatment of diseases which may be associated with particular isozymes. Godson et al. (*J. Biol. Chem.* 268:11946–11950 (1993)) disclosed use of stable transfection of antisense PKC-α cDNA in cytomegalovirus promotor-based expression vectors to specifically decrease expression of PKC-α protein by approximately 70%. It was demonstrated that this inhibition caused a loss of phospholipase $A_2$-mediated arachidonic acid release in response to the phorbol ester PMA. Attempts by the same researchers at inhibiting PKC activity with oligodeoxynucleotides were ultimately unsuccessful due to degradation of oligonucleotides. Ahmad et al. disclose that transfection of the human glioblastoma cell line, U-87, with vectors expressing antisense RNA to PKCα inhibits growth of the glioblastoma cells in vitro and in vivo (Ahmad et al., *Neurosurg.* 35:904–908 (1994)). Diaz-Meco Conde et al. disclose a peptide corresponding to the pseudo-substrate region of PKC-ζ and oligonucleotides antisense to this isozyme (Wo Application 93/20101). Alvaro et al. have identified a novel mutant form of PKC associated with tumors and disclose oligonucleotide sequences complementary to the mutant form (WO Application 94/29455).

SUMMARY OF THE INVENTION

In accordance with the present invention, oligonucleotides are provided that are specifically hybridizable with a nucleic acid that encodes PKCα and are capable of inhibiting PKCα expression. This relationship is commonly denominated as "antisense". The oligonucleotides contain a methoxyethoxy (—O—$CH_2CH_2OCH_3$) modification at the 2' position of the sugar moiety of at least one nucleotide. These oligonucleotides, referred to herein as "2'-methoxyethoxy" or "2'-O—$CH_2CH_2OCH_3$" compounds, have been found to be surprisingly more potent than previously tested oligonucleotides for inhibiting PKC expression. They are believed to be useful both diagnostically and therapeutically, and are believed to be particularly useful in the methods of the present invention.

Also provided are methods for modulating the expression of PKCα using the oligonucleotides of the invention. These methods are believed to be useful both therapeutically and diagnostically as a consequence of the relationship between PKCα and inflammation and hyperproliferation.

Other aspects of the invention are directed to methods for diagnostics and treatment of conditions associated with PKCα.

BRIEF DESCRIPTION OF THE DRAWINGS

FIG. 1A shows the effect of ISIS 9605 compared to the deoxyphosphorothioate compound, ISIS 3521. FIG. 1B shows the effect of ISIS 9606 compared to the deoxyphosphorothioate compound, ISIS 3521.

FIGS. 5A and 5E are line graphs showing the effects of once daily treatment with oligonucleotides having SEQ ID NO: 1 on growth of human colon carcinoma (Colo 205) tumor xenografts subcutaneously transplanted in female Balb/c nude mice. FIG. 5A shows the effect of the deoxy-phosphorothioate compound, ISIS 3521.

DETAILED DESCRIPTION OF THE INVENTION

Figure 1A:
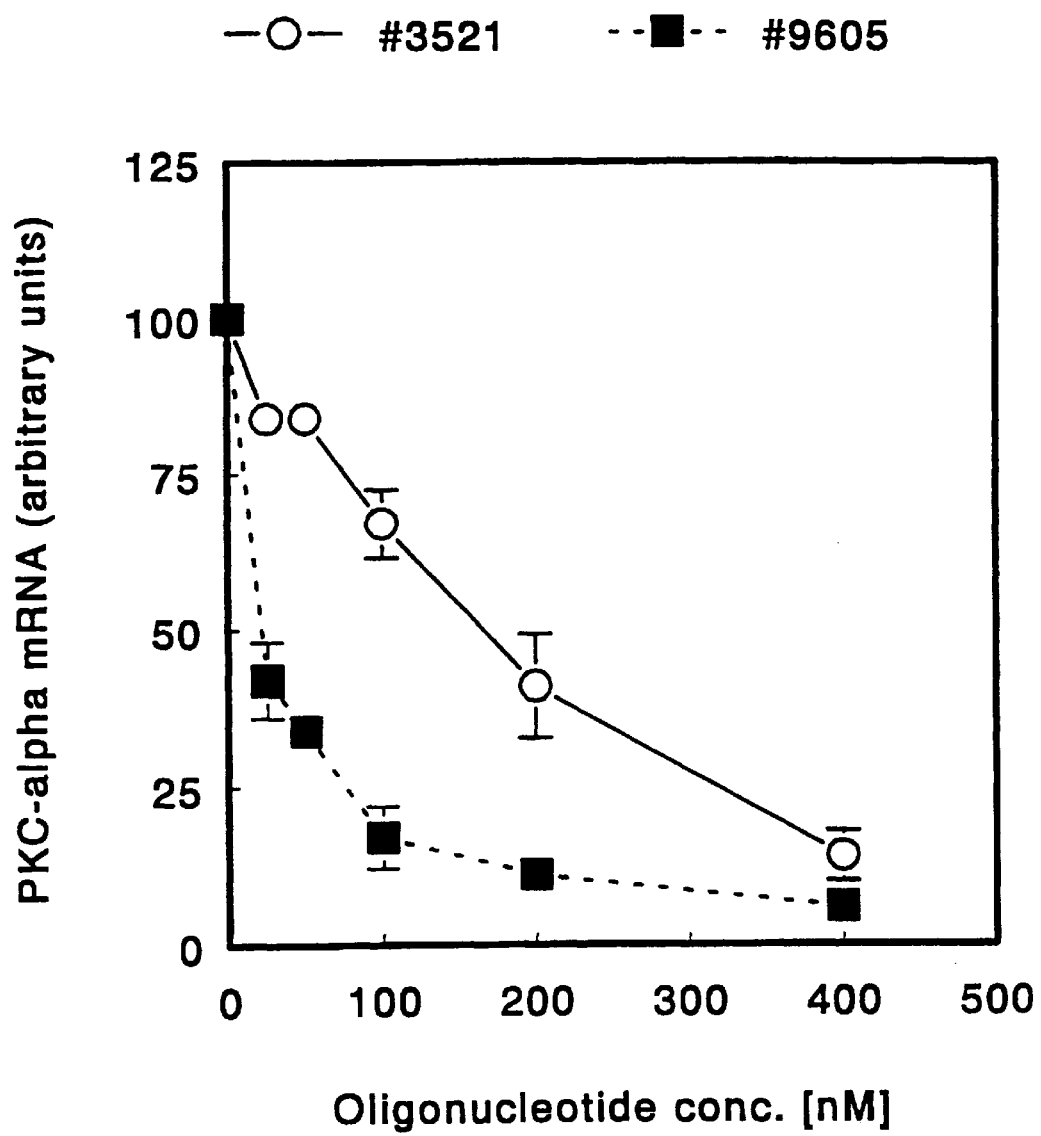
FIGS. 1A–1B are a set of line graphs showing the effect of 2'-methoxyethoxy modified oligonucleotides having SEQ ID NO: 1 on PKCα mRNA levels in A549 cells.

Oligonucleotides have been employed as therapeutic moieties for the treatment of disease states in animals and man. For example, workers in the field have now identified antisense, triplex and other oligonucleotide compositions which are capable of modulating expression of genes implicated in viral, fungal and metabolic diseases. A number of oligonucleotides are presently in clinical trials for a variety of indications including viral infections and inflammatory conditions.

Current agents which modulate the activity or metabolism of protein kinase C exhibit many unacceptable side effects due to their lack of specificity, or they exhibit only limited effectiveness in inhibiting the enzyme. The instant invention circumvents problems encountered by prior workers by modulating the production of the enzyme, rather than inhibiting the enzyme directly, to achieve the therapeutic effect. In the instant invention, the oligonucleotide is designed to bind directly to mRNA or to a gene, ultimately modulating the amount of PKC protein made from the gene.

This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding PKC; in other words, a PKC gene or mRNA expressed from a PKC gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of PKC gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Modifications may be on one or more bases, sugars, or backbone linkages, or combinations of these; such modifications are well known in the art. Modified or substituted oligonucleotides are often preferred over native forms because of properties such as, for example, enhanced cellular uptake and increased stability in the presence of nucleases.

The oligonucleotides may be chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one embodiment, a chimeric oligonucleotide comprises at least one region modified to increase target binding affinity, and, usually, a region that acts as a substrate for RNAse H. Affinity of an oligonucleotide for its target (in this case a nucleic acid encoding PKC) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PKC gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotide modifications which enhance target binding affinity are also, independently, able to enhance nuclease resistance.

The oligonucleotides of the present invention contain a methoxyethoxy (—O—CH$_2$CH$_2$OCH$_3$) modification at the 2' position of the sugar moiety of at least one nucleotide. This modification has been shown to increase both affinity of the oligonucleotide for its target and nuclease resistance of the oligonucleotide. Oligonucleotides in accordance with this invention can comprise a plurality of nucleotide subunits which each further comprise a methoxyethoxy (—O—CH$_2$CH$_2$OCH$_3$) modification at the 2' position of their sugar moiety. Thus, only one, a plurality, or all of the nucleotide subunits of the olignucleotides of the invention can comprise a methoxyethoxy (—O—CH$_2$CH$_2$OCH$_3$) modification at the 2' position of the sugar moiety. Oligonucleotides comprising a plurality of nucleotide subunits having a 2'-methoxyethoxy modification can have such a modification on any of the nucleotide subunits within the oligonucleotide. Oligonucleotides in accordance with this invention are preferably from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis (Martin, P., *Helv. Chim. Acta,* 1995, 78, 486–504). Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides. The intersugar linkages between the individual nucleotides of the oligonucleotides of the invention can be, but are not limited to, all phosphodiester linkages, all phosphorothioate linkages, or a mixture of both phosphodiester and phosphorothioate linkages. In addition, the oligonucleotides of the invention can comprise other intersugar linkages as known to the skilled artisan.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, a 5' cap region, an intron/exon junction, coding sequences or sequences in the 5'- or 3'-untranslated region.

The oligonucleotides of this invention are designed to be hybridizable with messenger RNA derived from the PKC gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the PKC gene.

The oligonucleotides of this invention can be used in diagnostics, therapeutics, prophylaxis, and as research reagents and in kits. Since the oligonucleotides of this invention hybridize to the PKC gene and its mRNA, sandwich and other assays can easily be constructed to exploit this fact. Furthermore, since the oligonucleotides of this invention hybridize specifically to particular isozymes of the PKC mRNA, such assays can be devised for screening of cells and tissues for particular PKC isozymes. Such assays can be utilized for diagnosis of diseases associated with various PKC forms. Provision of means for detecting hybridization of oligonucleotide with the PKC gene can routinely be accomplished. Such provision may include enzyme conjugation, radiolabelling or any other suitable detection systems. Kits for detecting the presence or absence of PKC may also be prepared.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish PKC-associated tumors, particularly tumors associated with PKCα, from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of PKC expression, particularly the specific expression of PKCα. For example, radiolabeled oligonucleotides can be prepared by $^{32}P$ labeling at the 5' end with polynucleotide kinase. Sambrook et al., *Molecular Cloning. A Laboratory Manual,* Cold spring Harbor Laboratory Press, 1989, Volume 2, p. 10.59. Radiolabeled oligonucleotides are then contacted with tissue or cell samples suspected of PKC expression and the sample is washed to remove unbound oligonucleotide. Radioactivity remaining in the sample indicates bound oligonucleotide (which in turn indicates the presence of PKC) and can be quantitated using a scintillation counter or other routine means. Radiolabeled oligo can also be used to perform autoradiography of tissues to determine the localization, distribution and quantitation of PKC expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing PKC. Quantitation of the silver grains permits PKC expression to be detected.

Analogous assays for fluorescent detection of PKC expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling Va., p. 21).

Each of these assay formats is known in the art. One of skill could easily adapt these known assays for detection of PKC expression in accordance with the teachings of the invention providing a novel and useful means to detect PKC expression, particularly of PKCα.

For therapeutic or prophylactic treatment, oligonucleotides are administered in accordance with this invention. Oligonucleotides may be formulated in a pharmaceutical composition, which may include pharmaceutically acceptable carriers, thickeners, diluents, buffers, preservatives, surface active agents and the like in addition to the oligonucleotide.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or by intravenous, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates. Optimum dosages may vary depending on the relative potency of individual oligonucleotides, and can generally be calculated based on EC50's in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is psoriasis, a reduction or ablation of the skin plaque is an indication that the administered dose has a therapeutic effect. Similarly, in mammals being treated for cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Oligonucleotide synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from PerSeptive Biosystems (Framingham, Mass.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, Ph 7.0.

Phosphorothioate oligonucleotides targeted to human PKCα were designed using the cDNA sequence published by Finkenzeller et al., *Nucl. Acids Res.* 18:2183 (1990); Genbank accession number X52479.

2'-O—$CH_2CH_2OCH_3$ modified oligonucleotides:

Oligonucleotides having 2'-O—$CH_2CH_2OCH_3$ modified nucleotides were synthesized according to the method of Martin. *Helv. Chim. Acta* 1995, 78,486–504. All 2'-O—$CH_2CH_2OCH_3$_ cytosines were 5-methyl cytosines.

5-Methyl cytosine monomers:

2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-Methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/Hexane (3:1) as the eluting solvent. The pure fractions were combined to give 90.6 g (87%) of the title compound.

Example 2

Cell culture and treatment with phorbol esters and oligonucleotides

PKC protein half-lives have been reported to vary from 6.7 hours to over 24 hours (Young et al., *Biochem. J.* 244:775–779 (1987); Ballester et al., *J. Biol. Chem.* 260:15194–15199 (1985)). These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., (Krug et al., *J. Biol. Chem.* 262:11852–11856 (1987)) lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 µl DOTMA (Lipofectin reagent, BRL, Bethesda, Md.) was added. Oligonucleotides were added to a concentration of 1 µM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 µM) were added and the cells were incubated at 37° C. for 24 hours.

Cells were washed three times in phosphate-buffered saline (PBS) and cellular proteins were extracted in 120 µl sample buffer (60 mM Tris pH 6.8, 2% SDS, 10% glycerol, 10 mM dithiothreitol) and boiled for 5 minutes. Intracellular levels of PKC-α protein were determined by immunoblotting.

Example 3

Effect of ISIS 3521 on PKC protein expression

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-α (UBI, Lake Placid N.Y.) diluted to 0.2 µg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine Calif.). Membranes were then washed extensively in TBS plus 0.2% nonfat milk. Bands were visualized and quantitated using a Phosphorimager (Molecular Dynamics, Sunnyvale, Calif.). PKC-α appears as a single band with a molecular weight of 80 kD.

Each oligonucleotide was tested three times, in triplicate, and the results of the experiments were normalized against percentage of protein present as compared to cells which were not treated with oligonucleotide. Oligonucleotide ISIS 3521 (5'-GTTCTCGCTGGTGAGTTTCA, SEQ ID NO: 1), targeted to the 3' untranslated region of PKCα, reduced PKC protein levels by approximately 48% compared to untreated controls.

Example 4

Effect of oligonucleotides having SEQ ID NO: 1 on PKC-α mRNA levels

A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale Calif.). ISIS 3521 (SEQ ID NO: 1) gave approximately 80% reduction of the smaller transcript and over 90% reduction of the larger transcript.

Figure 1B:
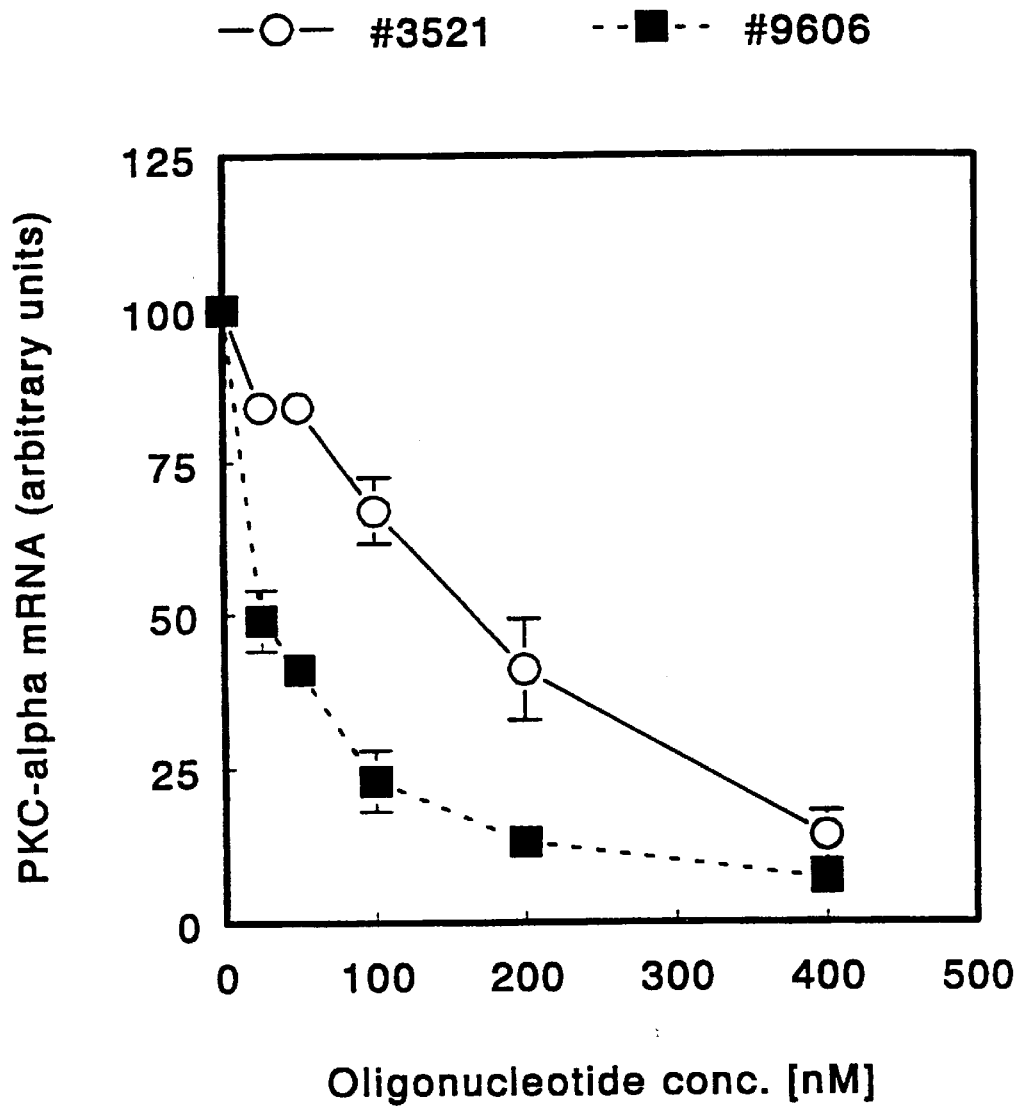

Two oligonucleotides having SEQ ID NO: 1 and an 8-deoxynucleotide central region flanked on each side by nucleotides having the 2'-O—CH$_2$CH$_2$OCH$_3$ modification were synthesized. For ease of synthesis, the last nucleotide was a deoxynucleotide. These compounds, shown in Table 1, differ in that one of them, ISIS 9606, has a uniform phosphorothioate backbone while the other, ISIS 9605, has a phosphorothioate backbone in the central region (backbone linkages 7–14) and a phosphodiester backbone in the remaining (flanking) regions. These oligonucleotides were tested for their ability to inhibit PKCα mRNA expression in A549 cells, in comparison to the phosphorothioate compound, ISIS 3521. The results are shown in FIGS. 1A and 1B. IC50s were calculated (oligonucleotide concentration yielding 50% inhibition) for the three compounds. The phosphorothioate compound, ISIS 3521, showed an IC50 of approximately 170 nM. Both the methoxyethoxy compounds, ISIS 9605 and 9606, showed IC50s of approximately 25 nM. This 6-to-7- fold increase in potency with the methoxyethoxy modification was an indication of surprising activity. Because of their extremely low IC50s, the 2'-methoxyethoxy compounds 9605 and 9606 are preferred.

TABLE 1

Oligonucleotides having SEQ ID NO: 1

| ISIS # | |
|---|---|
| 3521 | GsTsTsCsTsCsGsCsTsGsGsTsGsAsGsTsTsTsCsA |
| 9605 | GoToToCoToCsGsCsTsGsGsTsGsAsGoToToToCoA |

TABLE 1-continued

Oligonucleotides having SEQ ID NO: 1

| ISIS # | |
|---|---|
| 9606 | GsTsTsCsTsCsGsCsTsGsGsTsGsAsGsTsTsTsCsA |
| 12723 | GoToToCoToCsGsCsTsGsGsTsGsAsGoToToToCoA | bold = 2'-O—CH$_2$CH$_2$OCH$_3$
s = phosphorothioate (P=S) linkage
o = phosphodiester (P=O) linkage Example 5

Culture of human A549 lung tumor cells

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Cells were trypsinized and washed and resuspended in the same medium for introduction into mice.

Example 6

Effect of ISIS 3521 on the growth of human A549 lung tumor cells in nude mice

200 μl of A549 cells (5×10$^6$ cells) were implanted subcutaneously in the inner thigh of nude mice. ISIS 3521, a phosphorothioate oligonucleotide with SEQ ID NO: 1, was administered twice weekly for four weeks, beginning one week following tumor cell inoculation. Oligonucleotides were formulated with cationic lipids (DMRIE/DOPE) and given subcutaneously in the vicinity of the tumor. Oligonucleotide dosage was 5 mg/kg with 60 mg/kg cationic lipid. Tumor size was recorded weekly.

Figure 2:
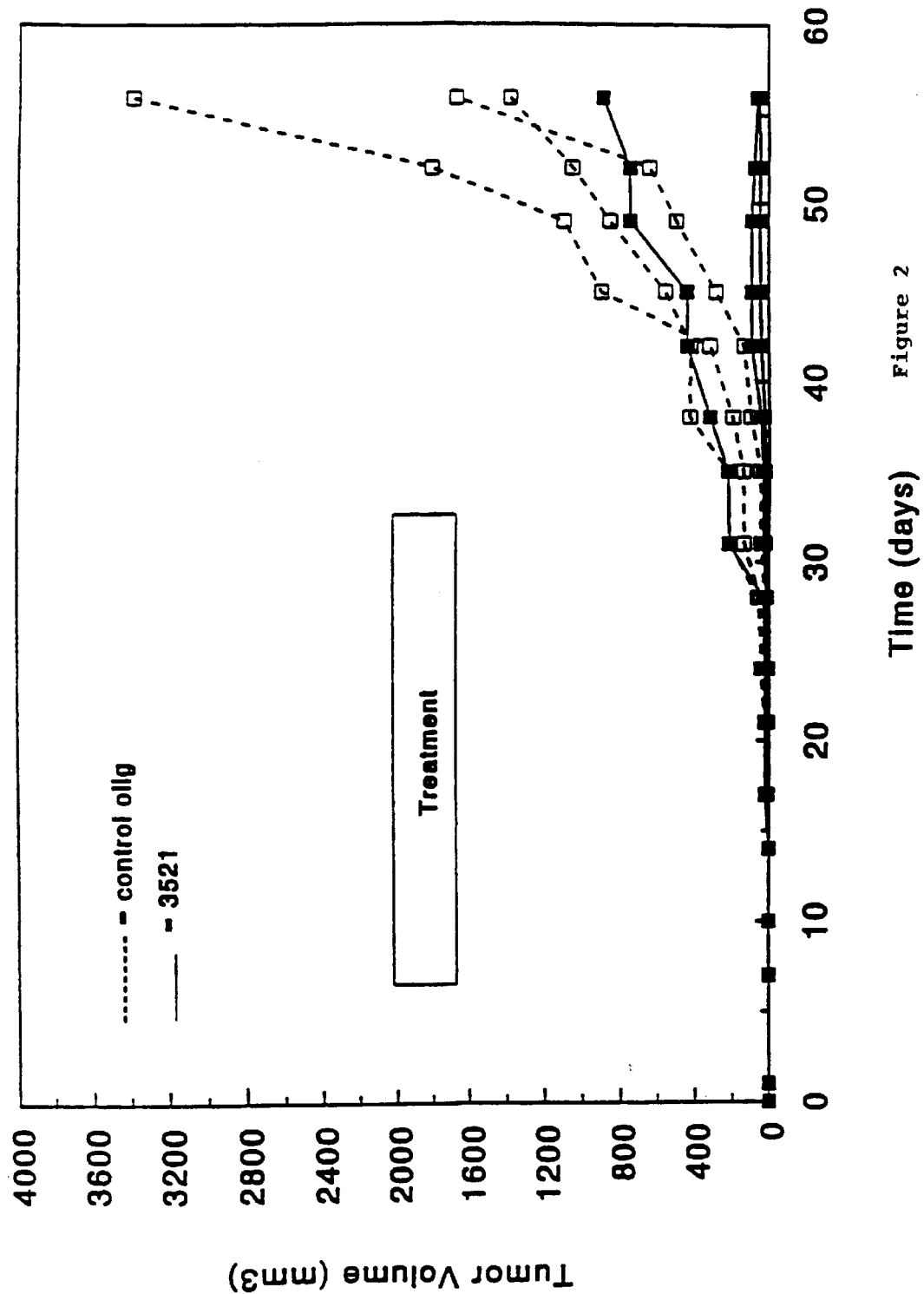
FIG. 2 is a line graph showing anti-tumor activity of ISIS 3521 on A549 tumor growth in nude mice. Each dashed line represents tumor volume in one animal treated with control oligonucleotide; each solid line represents tumor volume in one animal treated with ISIS 3521.

As shown in FIG. 2, tumor growth was almost completely inhibited in two of the three mice, and reduced compared to control levels in the third mouse. This inhibition of tumor growth by ISIS 3521 is statistically significant. The control oligonucleotide (ISIS 1082) is a 21-mer phosphorothioate oligonucleotide without significant sequence homology to the PKC mRNA target.

Administration of oligonucleotides to mice whose tumors had already reached detectable size had no discernable effect on subsequent tumor growth.

Example 7

Effect of ISIS 3521 on growth of human MDA-MB231 tumors in nude mice

Figure 3:
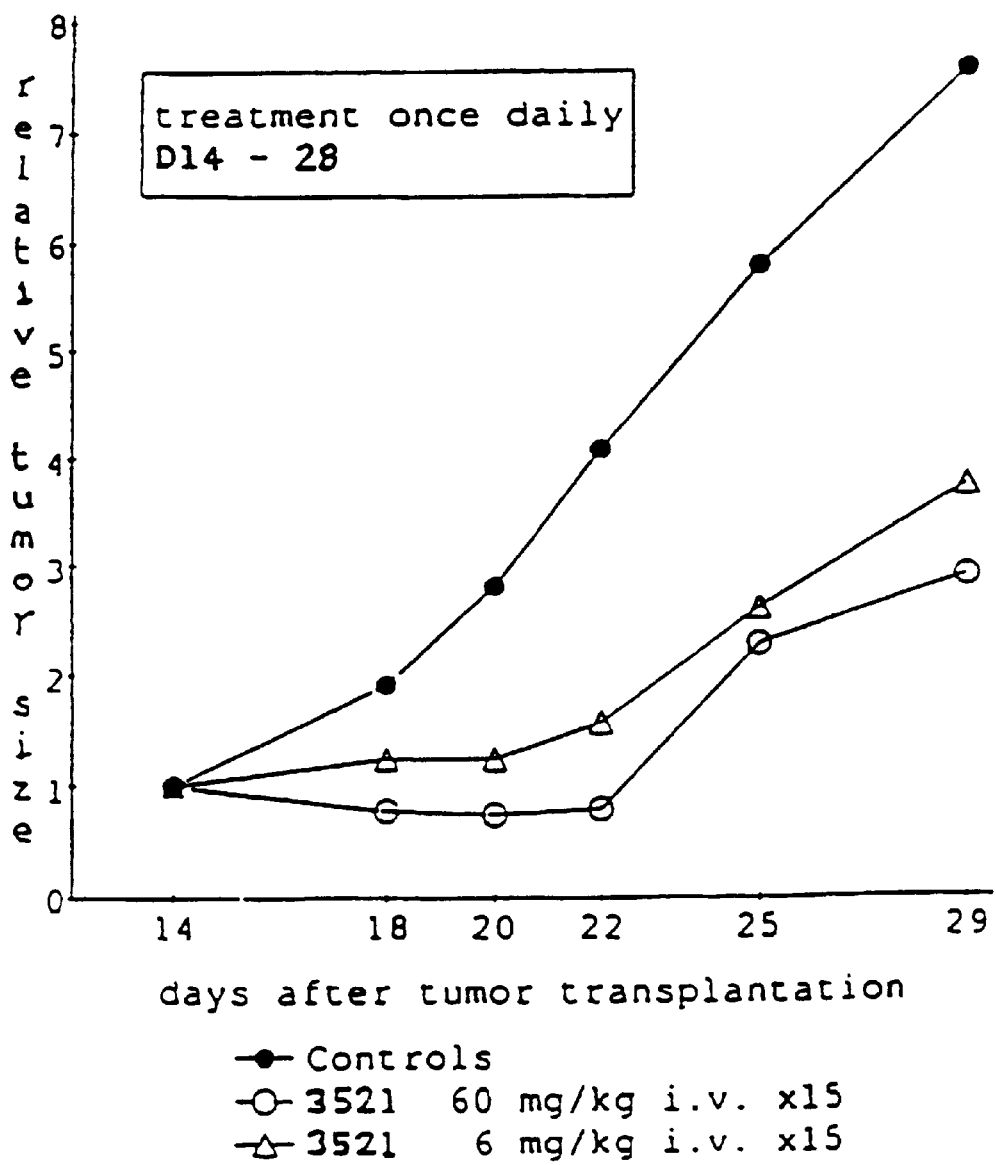
FIG. 3 is a line graph showing the effect of ISIS 3521 on growth of human MDA-MB231 tumors in nude mice. Each line represents tumor volume in one animal. ●=control; ○=oligonucleotide at 60 mg/kg; ∆=oligonucleotide at 6 mg/kg.

MDA-MB231 human breast carcinoma cells were obtained from the American Type Culture Collection (Bethesda, Md.). Serially transplanted MDA-MB231 tumors were established subcutaneously in nude mice. Beginning two weeks later, ISIS 3521 was administered intravenously, in saline, daily for 14 days at dosages of 60 mg/kg and 6 mg/kg. Control oligonucleotide ISIS 1082 was also administered at these doses, and a saline control was also given. Tumor growth rates were monitored for the two-week period of oligonucleotide administration. As shown in FIG. 3, ISIS 3521 significantly inhibited tumor growth at dosages of 60 mg/kg and 6 mg/kg. The control oligonucleotide (ISIS 1082) also showed some reduction in tumor growth, but this effect was less than with the antisense oligonucleotide even at high doses, and considerably less at the lower dose. A lower-dose study was conducted at 6 mg/kg and 0.6 mg/kg. At 0.6 mg/kg ISIS 3521 significantly reduced tumor growth.

Example 8

Effect of ISIS 3521 on the growth of murine Lewis lung carcinoma in mice

Serially transplanted murine Lewis lung carcinomas were established in mice. Oligonucleotides 3521 was administered intravenously every day for 14 days at doses of 6 mg/kg and 0.6 mg/kg. Tumor growth rates were monitored for the two-week period of oligonucleotide administration. As expected, this oligonucleotide, targeted to a human PKC sequences, had insignificant effects on the mouse-derived tumors.

Example 9
Effects of antisense oligonucleotide ISIS 4189 on endogenous PKC-α expression in hairless mice In order to study oligonucleotide effects on endogenous PKC mRNA levels in normal animals, it was necessary to employ an oligonucleotide complementary to the murine PKC-α. ISIS 4189 is a 20-mer phosphorothioate oligonucleotide targeted to the AUG codon of mouse PKC-α. This region is without homology to the human PKC sequence and the oligonucleotide has no effect on expression of PKC-α in human cells. ISIS 4189 has an IC50 of 200 nM for mRNA reduction in C127 mouse breast epithelial cells. ISIS 4189 in saline was administered intraperitoneally to hairless mice at concentrations of 1, 10 or 100 mg/kg body weight. Injections were given daily for seven days. Tissues from liver, kidney, spleen, lung and skin were removed and PKC-α mRNA and protein levels were determined. Histopathological examination was also performed on liver, kidney and lung samples. ISIS 4189 at 100 mg/kg inhibited endogenous PKC-α mRNA levels in the mouse liver to 10–15% of control (saline) levels.

Example 10
Effect of ISIS 3521 on the growth of human T24 bladder tumors in nude mice Subcutaneous human T24 bladder carcinoma xenografts in nude mice were established by injection of $5 \times 10^6$ T24 cells under the skin. Mice were treated with ISIS 3521 or ISIS 4559, a phosphorothioate scrambled version of the ISIS 3521 sequence, or ISIS 1082, an unrelated control phosphorothioate oligonucleotide targeted to Herpes simplex virus (oligonucleotide doses 0.006 mg/kg, 0.06 mg/kg, 0.6 mg/kg or 6.0 mg/kg) or saline administered intraperitoneally three times weekly. By day 21, neither ISIS 1082 nor ISIS 4559 had any effect on tumor growth at any dose. By day 21, ISIS 3521 showed a dose-dependent inhibition of tumor growth at all dose levels, with a maximal inhibition of 90% at the 6 mg/kg dose.

Example 11
Effect of ISIS 3521 on the growth of human Colo-205 colon tumors in nude mice Subcutaneous human Colo-205 colon carcinoma xenografts in nude mice were established by injection of $5 \times 10^6$ Colo-205 cells under the skin. Mice were treated with ISIS 3521 and an unrelated control phosphorothioate oligonucleotide (ISIS 1082) administered intravenously once per day at a dosage of 6.0 mg/kg. In this study, ISIS 3521 inhibited tumor growth after 25 days by 84% compared to saline controls. The control oligonucleotide, ISIS 1082, inhibited tumor growth by 20%.

Example 12
Effect of ISIS 3521 on U-87 human glioblastoma subcutaneous xenografts into nude mice The U-87 human glioblastoma cell line was obtained from the ATCC (Rockville Md.) and maintained in Iscove's DMEM medium supplemented with heat-inactivated 10% fetal calf serum. Nude mice were injected subcutaneously with $2 \times 10^7$ cells. Mice were injected intraperitoneally with ISIS 3521 at dosages of either 2 mg/kg or 20 mg/kg for 21 consecutive days beginning 7 days after xenografts were implanted. Tumor volumes were measured on days 14, 21, 24, 31 and 35. On day 35 (7 days after end of treatment), ISIS 3521 at 2 mg/kg had reduced tumor volume by 84% compared to saline or sense oligonucleotide control. The 20 mg/kg dose reduced tumor size by 91% on day 35.

Example 13
Effect of ISIS 3521 on PKC-α protein levels in U-87 glioblastoma xenograft in nude mice PKCα protein levels in subcutaneous U-87 tumor xenografts were measured by Western blot analysis on day 24 (day 17 of treatment with ISIS 3521) and day 35 (7 days after end of treatment with ISIS 3521). An affinity-purified PKCα-specific polyclonal antibody (Life Technologies, Inc.) was used as the primary antibody. By day 24, ISIS 3521 was found to virtually totally abolish PKCα in the tumors. By seven days after cessation of oligonucleotide treatment (day 35), PKCα had returned to control levels.

Figure 4:
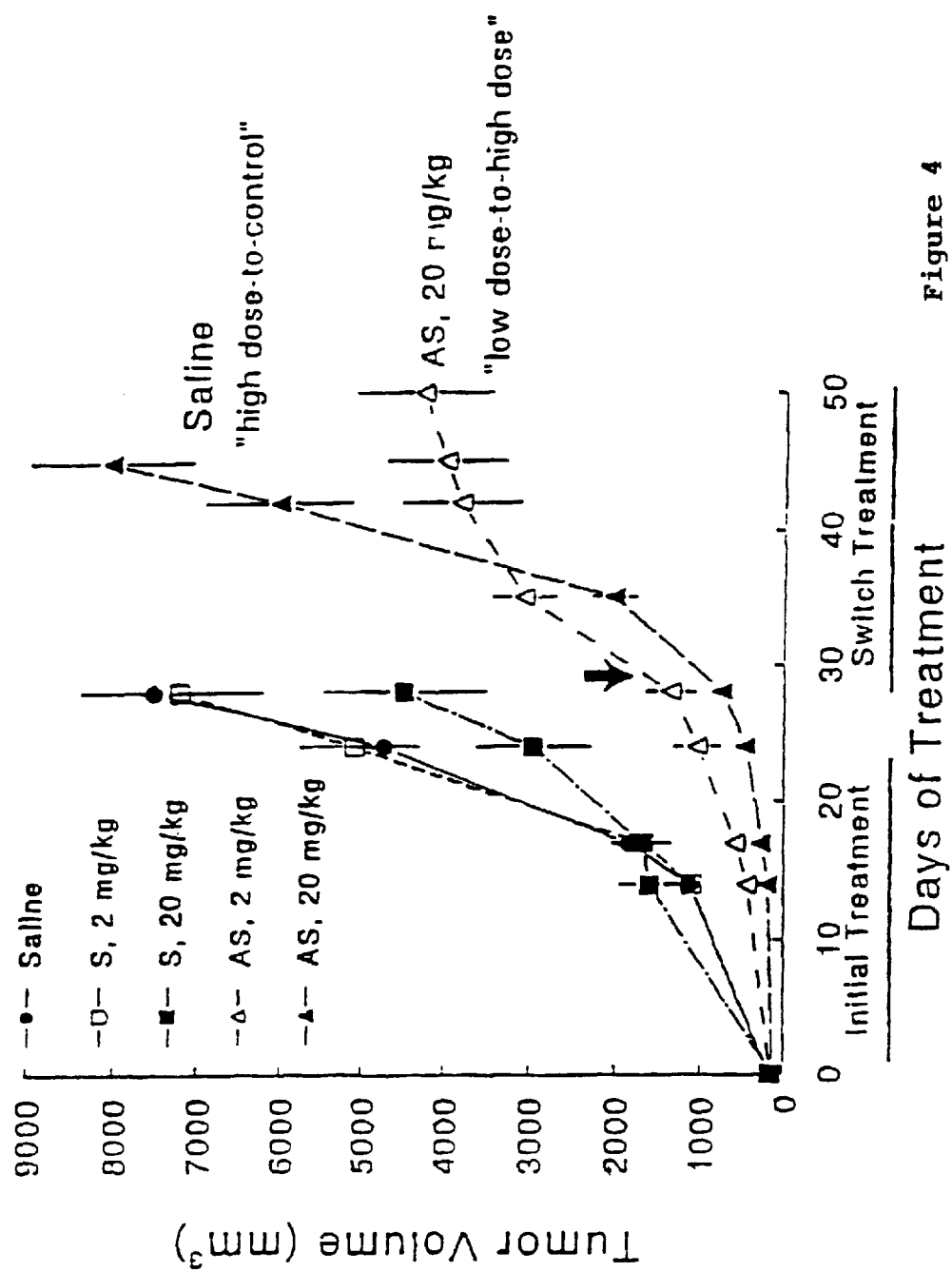
FIG. 4 is a line graph showing a "crossover" experiment to evaluate the effect of ISIS 3521 on U-87 glioblastoma cells in nude mice in vivo. The experiment was carried out with oligonucleotide doses of 2 mg/kg and 20 mg/kg and then treatment was switched (arrow). The group which had originally received ISIS 3521 at 20 mg/kg ("high dose-to-control" group, closed triangles) then received saline and the group which had originally received ISIS 3521 at 2 mg/kg ("low dose-to-high dose", open triangles) then received ISIS 3521 at 20 mg/kg. S=sense oligonucleotide (control); AS=antisense oligonucleotide (ISIS 3521) targeted to PKCα.

Example 14
"Crossover experiment" to evaluate effect of switching treatment on tumor size The two groups of mice with subcutaneous U-87 xenografts previously treated with ISIS 3521 (2 mg/kg or 20 mg/kg) were switched to different treatments on day 35 (7 days after the initial 21 day treatment had ended). The group which had previously received 20 mg/kg ISIS 3521 now received saline ("high dose-to-control"). The group which had received 2 mg/kg ISIS 3521 now received 20 mg/kg ISIS 3521 ("low dose-to-high dose"). This crossover treatment was continued for 21 days as for the original treatment. As shown in FIG. 4, the growth of the tumors in the "low dose-to-high dose" group (open triangles) leveled off after treatment was switched (arrow). The growth of the tumors in the "high dose-to-control" group (closed triangles) rapidly accelerated after switching to saline treatment (arrow). S=sense oligonucleotide (control); AS=antisense oligonucleotide (ISIS 3521) targeted to PKCα.

Example 15
Effect of ISIS 3521 on intracerebral U-87 glioblastoma xenografts into nude mice U-87 cells were implanted in the brains of nude mice. Mice were treated via continuous intraperitoneal administration of antisense oligonucleotide ISIS 3521 (20 mg/kg), control sense oligonucleotide (20 mg/kg) or saline beginning on day 7 after xenograft implantation. All mice survived until day 25, at which point the saline-treated mice began to die. All saline-treated mice and sense oligonucleotide-treated mice were dead by day 41. In contrast, all ISIS 3521-treated mice were alive until approximately day 37, and half of the mice were still alive at day 61. At the termination of the experiment at day 80, 40% of the ISIS 3521-treated mice were still alive.

Figure 5A:
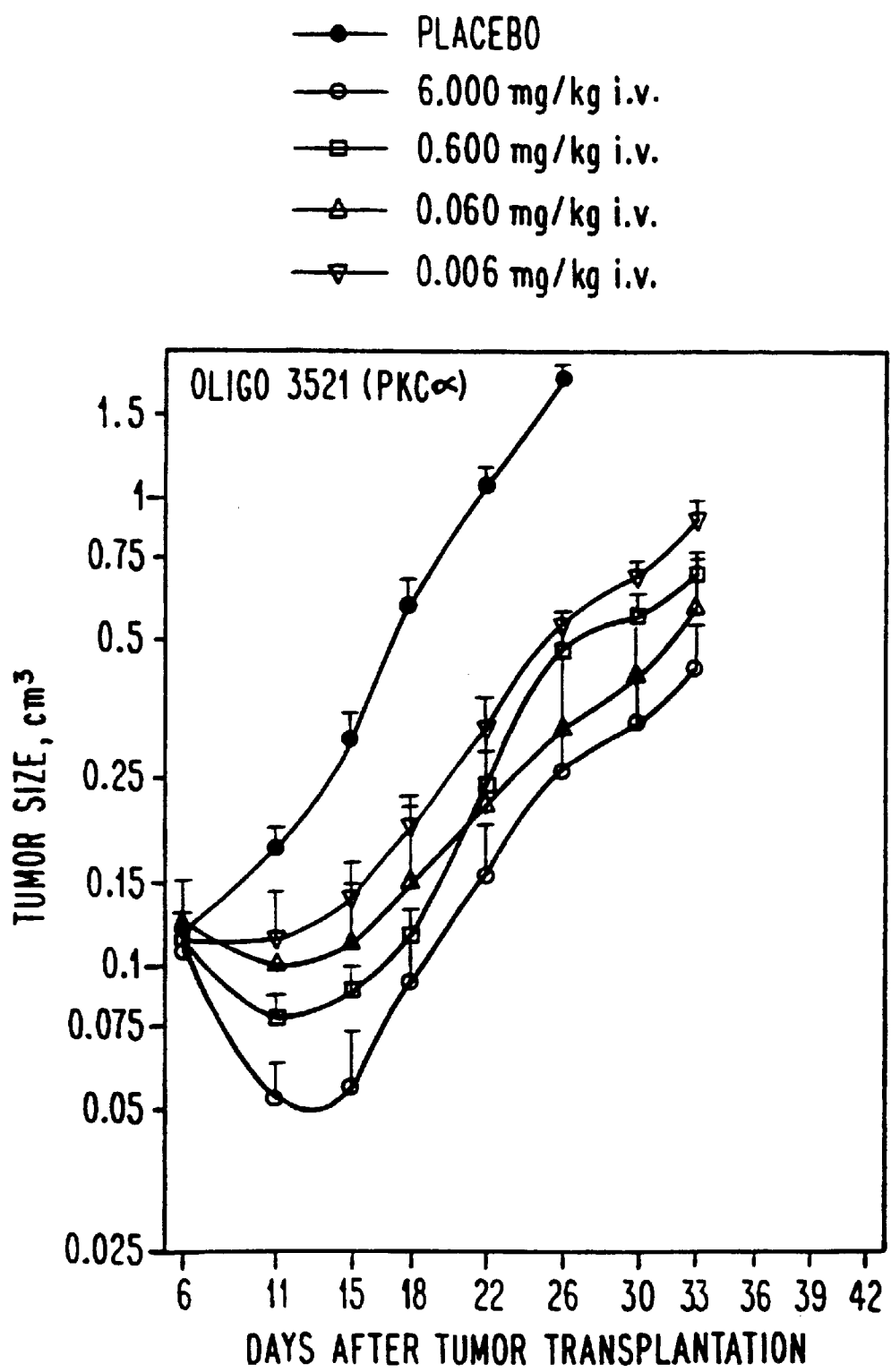
Figure 5B:
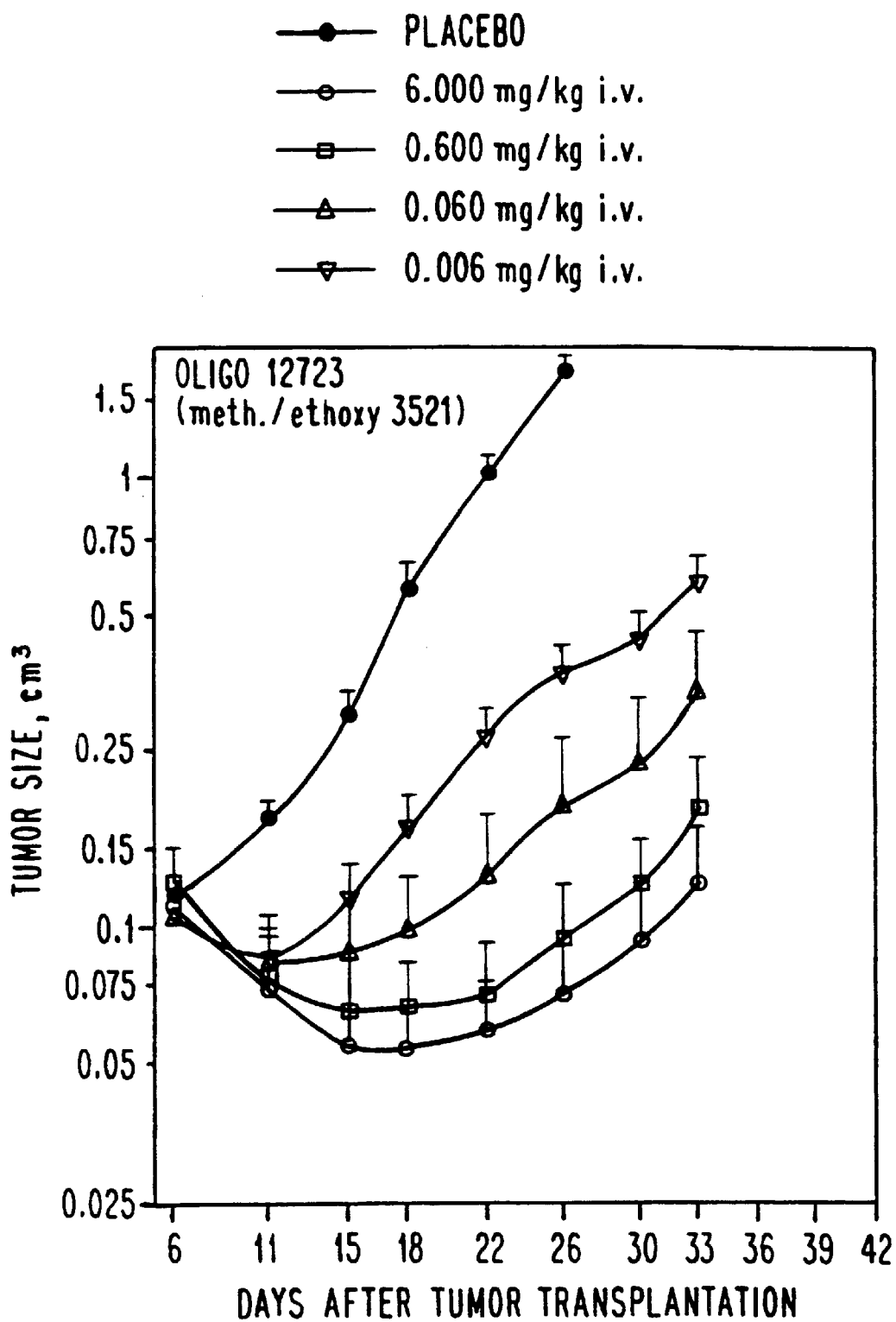
FIG. 5B shows the effect of the 2'-methoxyethoxy modified compound, ISIS 12723.

Example 16
Effect of the 2'-methoxyethoxy oligonucleotide ISIS 12723 on the growth of human Colo-205 colon tumors in nude mice Subcutaneous human Colo-205 colon carcinoma xenografts in nude mice were established by injection of $5 \times 10^6$ Colo-205 cells under the skin. Mice were treated with ISIS 12723 (SEQ ID NO: 1 with an 8-deoxynucleotide central region flanked on each side by six nucleotides having the 2'-O-CH$_2$CH$_2$OCH$_3$ modification, a phosphorothioate backbone in the central region (backbone linkages 7–14) and a phosphodiester backbone in the remaining (flanking) regions) or ISIS 3521 (SEQ ID NO: 1, fully deoxy phosphorothioate), administered intravenously once per day at a dosage of 0.006, 0.06, 0.6 or 6.0 mg/kg. As shown in FIG. 5, in this study, ISIS 12723 inhibited tumor growth by over 95% compared to saline placebo controls. ISIS 3521 inhibited tumor growth by over 83% compared to controls. The methoxyethoxy compound, ISIS 12723, is therefore preferred.

What is claimed is:

1. An oligonucleotide comprising SEQ ID NO: 1, wherein at least one nucleotide of said oligonucleotide comprises a 2'-O—CH$_2$CH$_2$OCH$_3$ modification of its sugar moiety.

2. The oligonucleotide of claim 1, wherein the intersugar linkages between each of the nucleotides of SEQ ID NO: 1 are phosphorothioate linkages.

3. The oligonucleotide of claim 1, wherein the intersugar linkages between each of the nucleotides of SEQ ID NO: 1 are phosphodiester linkages.

4. The oligonucleotide of claim 1, wherein the intersugar linkages between each of the nucleotides of SEQ ID NO:1 are a mixture of phosphodiester linkages and phosphorothioate linkages.

5. A method of inhibiting PKC expression in cells comprising contacting the cells with an oligonucleotide of claim 1.

6. The method of claim 5 wherein the cells are cancer cells.

7. A method of treating a condition associated with expression of PKC comprising administering to an animal, cells, tissues, or a bodily fluid thereof, a therapeutically effective amount of an oligonucleotide of claim 1.

8. The method of claim 7 wherein said condition is an inflammatory or hyperproliferative disorder.

9. The method of claim 8 wherein the condition is cancer or psoriasis.

\* \* \* \* \*